US012697438B2

(12) United States Patent
Fech et al.

(10) Patent No.: US 12,697,438 B2
(45) Date of Patent: Aug. 4, 2026

(54) APPLICATOR WITH DOSING UNIT

(71) Applicant: Erbe Elektromedizin GmbH, Tuebingen (DE)

(72) Inventors: Andreas Fech, Tuebingen (DE); Frederik Kleber, Wannweil (DE); Walter Linzenbold, Boeblingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 927 days.

(21) Appl. No.: 17/881,206

(22) Filed: Aug. 4, 2022

(65) Prior Publication Data

US 2023/0050388 A1    Feb. 16, 2023

(30) Foreign Application Priority Data

Aug. 10, 2021    (EP) ..................................... 21190627

(51) Int. Cl.
*A61M 5/30*        (2006.01)
*A61M 3/02*        (2006.01)
*A61M 39/26*       (2006.01)

(52) U.S. Cl.
CPC ............ *A61M 5/30* (2013.01); *A61M 3/0216* (2014.02); *A61M 39/26* (2013.01)

(58) Field of Classification Search
CPC ...... A61M 5/30; A61M 3/0216; A61M 39/26; A61M 5/2053; A61M 2202/09; A61M 2205/3337; A61M 5/2448; A61M 2005/2433; A61M 5/3007; A61M 5/31576; A61M 2005/31588; A61M 2250/00
See application file for complete search history.

(56) References Cited

U.S. PATENT DOCUMENTS

| | | | |
|---|---|---|---|
| 2002/0183738 A1 | 12/2002 | Chee et al. | |
| 2005/0085767 A1* | 4/2005 | Menassa ................. | A61M 5/30 604/68 |
| 2007/0191758 A1* | 8/2007 | Hunter ................... | A61B 17/20 604/164.01 |
| 2013/0102957 A1 | 4/2013 | Hunter et al. | |
| 2016/0184524 A1* | 6/2016 | Fech ..................... | A61M 39/22 604/500 |
| 2016/0184525 A1 | 6/2016 | Fech et al. | |
| 2020/0306450 A1 | 10/2020 | Enderle et al. | |

FOREIGN PATENT DOCUMENTS

| | | |
|---|---|---|
| EP | 3015076 A1 | 5/2016 |
| JP | 2016123863 A | 7/2016 |
| JP | 2016533859 A | 11/2016 |
| RU | 2650584 C2 | 4/2018 |
| WO | 2013076151 A1 | 5/2013 |

* cited by examiner

*Primary Examiner* — Theodore J Stigell
(74) *Attorney, Agent, or Firm* — Blank Rome LLP

(57) ABSTRACT

An instrument having a dosing unit connected to a handle or housing of instrument. The dosing unit may include a reusable actuator with a drive unit and a single-use cartridge. The Cartridge may have a cylinder and a piston, and may be filled by a user prior to the intervention or may be prefilled by the manufacturer. The dosing unit is brought into an open position offset from housing by, for example, operating a latch slider and pulling the dosing unit in a proximal direction. After insertion of the cartridge, the dosing unit may be moved toward housing and the latched slider will lock the dosing unit into a closed position.

16 Claims, 3 Drawing Sheets

APPLICATOR WITH DOSING UNIT

CROSS-REFERENCE TO RELATED APPLICATION

This application claims priority to European Application No. 21190627.6, filed Aug. 10, 2021, the entirety of which is incorporated by reference herein.

TECHNICAL FIELD

Embodiments of the invention described herein relate to an instrument for application of a medical liquid in an animal or human body, an apparatus for operating the instrument, and a method for creation of a fluid flow from two different fluids.

BACKGROUND

For needleless injection of medicines as well as other medical effective liquids into tissue of human or animal bodies, devices are used that use a fluid provided under high pressure for penetration of the skin of the patient and for needleless creation of a penetration channel in which then a treatment fluid under low pressure is introduced.

From EP 3 015 076 A1 an applicator is known by means of which a treatment fluid, e.g. a styptic liquid, is atomized by means of pressurized air or another gas being under pressure and can be applied onto the area to be treated in this manner. The applicator comprises a holder having a fluid channel in which a valve is arranged and which can be connected to a gas pressure source. The fluid channel opens out at an atomizing nozzle. A common syringe can be attached to the applicator. If the user holds the applicator in his/her hands, he can release the valve for the air channel with one finger and can actuate the plunger of the syringe with his/her thumb, such that the liquid contained in the syringe is guided to the atomizing nozzle and is discharged there in form of spray.

In addition, US 2013/0102957 A1 discloses an instrument for a needleless injection of a substance into a body. The instrument comprises a reservoir for storing the substance to be injected that is connected to an injection nozzle via a fluid channel. For discharging of the treatment fluid in a short sharp jet, an electrodynamic drive is assigned to a plunger arranged in the reservoir that creates a fluid pressure progress at the injection nozzle with a very steep front flank. The pressure increase generates a sharp liquid jet that is suitable for penetration of the skin. After the steep pressure increase the pressure drops down to a lower level for inserting the liquid into the tissue, in order to finally resume to zero after termination of the operating cycle.

In addition, for needleless injection of treatment liquids, EP 3 714 926 A1 proposes an instrument having multiple fluid channels that channel different liquids to an injection nozzle. Particularly it is provided to have a central channel for an injection fluid for opening a penetration channel, wherein the central channel is surrounded by a second channel by means of which treatment fluid is channeled toward the injection nozzle.

The instrument is basically well suitable for being used on patients. However, thereby the channel provided for the treatment fluid has to be completely filled with this fluid. If a patient-specific treatment fluid is used, a fluid amount of treatment fluid has to be provided that is larger than the fluid amount to be applied to the patient.

This also applies for the system according to EP 3 040 101 B1 from which an instrument with two fluid channels is known. A first channel guides an injection fluid and a second channel a treatment fluid to an application nozzle. For supply, an apparatus having a pressure reservoir and multiple valves is provided that particularly supplies the injection fluid with a predefined pressure regime to the instrument.

SUMMARY

It is the object of embodiments of the invention to provide an improved concept for needleless application of treatment fluids.

The instrument according to embodiments of the invention serves for injection of a medical liquid in an animal or human body, whereby the instrument is configured to apply two different fluids. A first fluid serves for needleless opening of a channel in a tissue to be treated (penetration channel) and is ejected with a pressure impulse that has a steep pressure increase at its front flank. The instrument further comprises a dosing unit having a compartment for a fluid container with the second fluid. The second fluid is preferably a treatment fluid, e.g. a medicinal liquid, a cell suspension or any other liquid serving for treatment of a human or animal body or tissue. The dosing unit comprises a drive unit by means of which the fluid container can be put under pressure or can be specifically reduced in volume. For example, the fluid container can be specifically influenced by means of the drive unit, such that the volume of the fluid container is reduced in order to softly discharge the second fluid.

After the fluid container is arranged in the dosing unit directly on the instrument, dead volumina are minimized. In doing so losses of treatment liquid are avoided that are particularly undesired during use of patient-specific treatment liquid. Also the preparation of the instrument as well as the preparation of the supplying apparatus are simplified. The danger is minimized that residuals of a treatment liquid of a previous treatment remain in channels, pumps or valves and thus to contaminate the treatment liquid of a subsequent patient.

The control and discharge of first fluid and second fluid by means of one and the same apparatus allows a coordinated and careful fluid discharge. For example, the second fluid can contain living cells that must neither be subject to high pressure variations nor shear forces and that can be applied particularly careful with the embodiments of the instrument and apparatus described herein.

The dosing unit can be releasably attached to the instrument. Thereby it is particularly advantageous, if the dosing unit itself does not comprise a part that gets into contact with the first or second fluid. For example, the dosing unit can consist of a housing having a compartment for the fluid container and having a drive unit for force or pressure application on the fluid container. If the dosing unit is removed from the instrument, the instrument can be sterilized or can also be completely replaced without the need to replace the dosing unit. The dosing unit can be reused. If required, it can be cleaned and also sterilized.

The instrument can have a shank that comprises a bendable section at its distal end, wherein for control of the bend of the shank, an operating element can be provided on the housing. Such an instrument is suitable, for example, for insertion into a ureter or another body lumen and for injection of carrier liquid containing living cells, for example into a sphincter. For this purpose the fluid channel can comprise a jet-focusing exit opening at its distal end.

A valve arrangement can be provided in the housing of the instrument in order to create a fluid high pressure impulse in the fluid channel. However, this valve arrangement can also be part of an apparatus supplying the instrument.

While the first fluid is channeled from the apparatus via a hose to the instrument, the dosing unit can be connected with the instrument via an electrical line. The control of the dosing unit is then carried out by means of the apparatus to which the instrument is connected.

The housing of the instrument can comprise a fluid connector for the fluid container and a mechanical plug connector for a plug device provided on the dosing unit. In doing so, the fluid container, e.g. in the form of a cartridge or syringe, can be fluidically connected with the housing and can project into the dosing unit for mechanical actuation. Thereby, it is advantageous, if the plug device and the plug connector comprise corresponding operation directions. This results in that the dosing unit concurrently presses the fluid container against the fluid connector and thereby establishes a fluid connection when the dosing unit is plugged on the housing, if the fluid container is inserted into the compartment. For example, the fluid container can be a cartridge or any other container with movable plunger.

The drive unit of the dosing unit comprises preferably an actuating motor, e.g. a stepper motor, that is arranged to influence the fluid container via a gear. For example, the gear is a spindle-type gear that transfers the rotation movement of the actuating motor in a linear movement by means of which a plunger that is part of the fluid container can be moved specifically and in a controlled manner. By means of a respective control of the actuating motor, the output of the drive unit acting on the fluid container can be moved along a defined distance length, whereby a defined liquid amount is discharged.

For supply of the instrument an apparatus can be provided that comprises a control unit that is configured to initiate discharge of the first fluid with a first high pressure impulse first and subsequently with lower pressure and that is further configured to activate the dosing unit after the high pressure impulse for creating a low pressure impulse in order to discharge the second fluid with less pressure via the fluid channel.

With this concept a channel is opened in the tissue by means of the first fluid. In the further time progress after attenuation of the first pressure impulse, the treatment liquid (the second fluid) is channeled into the first fluid in order to be carefully introduced into the tissue. The apparatus can provide the first fluid in a pressure container from which it can be output in impulses by means of a quickly switching valve. In addition, the apparatus can have an electrical connector for the dosing unit of the instrument.

BRIEF DESCRIPTION OF THE DRAWINGS

Further details of advantageous embodiments of the invention are subject to the drawing or the description as well as dependent claims. The drawings show:

DETAILED DESCRIPTION

Figure 1:
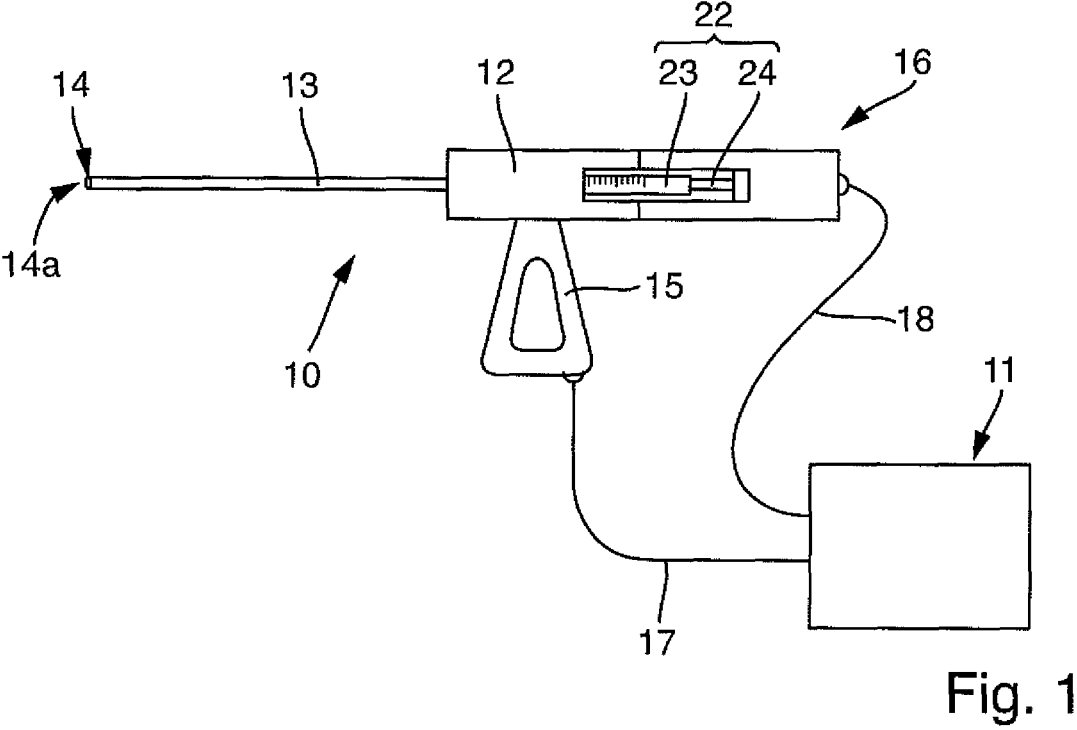
FIG. 1 an instrument according to an embodiment of the invention and a supplying apparatus in a schematic basic illustration, FIG. 2 a modified embodiment of the instrument in a schematic basic illustration, FIG. 3 the dosing unit of the instrument according to FIG. 1 or 2 in a longitudinally cut illustration in part, FIG. 4 an interface between the instrument and the dosing unit in a longitudinally cut basic illustration, FIG. 5 a functional plan of the instrument and an apparatus according to FIGS. 1 and 2, and FIG. 6 the pressure increase illustrated in an idealized manner during discharge of the first and second fluid in the form of a diagram.

An instrument 10 for injection of a medical liquid in a human or animal body, particularly for needleless injection of such a liquid into tissue of the body, is illustrated in FIG. 1. The instrument 10 is connected to an apparatus 11 serving for supply in order to supply the instrument with energy and/or media, e.g. sodium chloride solution.

The instrument 10 comprises a housing 12 from which a shank 13 extends in distal direction up to its distal end 14 at which an injection opening 14a is arranged in order to output a fluid jet. On housing 12, a handle 15 can be provided for manual guidance of instrument 10.

For treatment of the patient, e.g. for outputting medical fluid that is to be injected into its tissue, instrument 10 is in addition provided with a dosing unit 16 for this purpose. The dosing unit 16 can be arranged at any suitable site of housing 12, e.g. on a lateral side, on its top side, in a handle 15 or, as illustrated in FIG. 1, on its proximal back side opposite shank 13.

The instrument 10 provided for needleless injection of medical liquid in living tissue uses a first fluid for opening a penetration channel in the tissue. It is a liquid that is to be applied with high pressure that can be supplied by apparatus 11 via a fluid line 17 via which apparatus 11 is connected with instrument 10.

A second fluid, e.g. a medically effective liquid, is introduced specifically in the tissue of the patient by means of the dosing unit. For control of the dosing unit 16, apparatus 11 can be connected with instrument 10 via an electrical line 18 that is realized by means of a two- or multicore cable, for example.

For activation of instrument 10, a switch can be provided thereon that is then connected via a not illustrated control line or another control connection with apparatus 11. Alternatively, also other switches can be used, such as a foot switch or the like.

Figure 2:
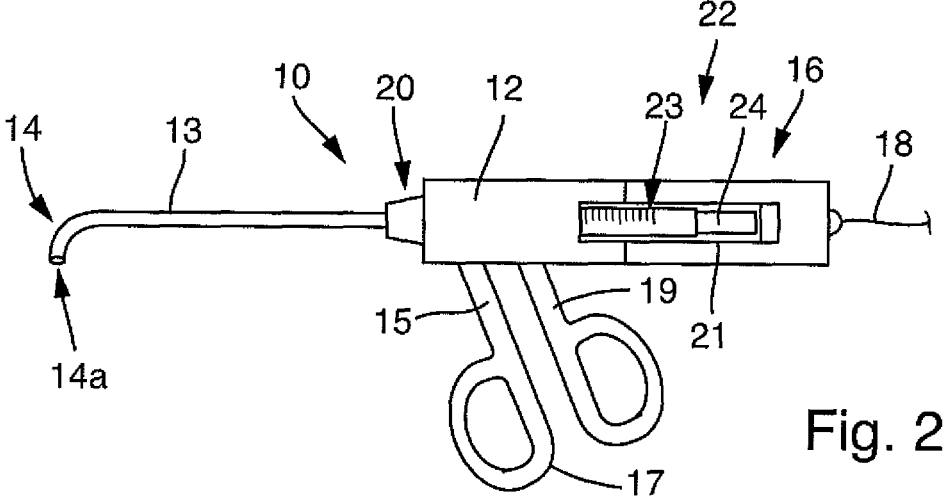

The instrument 10 that is illustrated in FIG. 1 in a particularly simple form can have additional functionalities, such as a bendable distal end 14, whereby the bending can be effected by means of a control lever 19, for example. Control lever 19 can be arranged in the vicinity of handle 15 or also at another site of instrument 10. It is in addition possible to arrange shank 13 on housing 12 rotatably, whereby a respective slewing connector 20 can be provided for this purpose. Apart therefrom, the explanations referring to instrument 10 according to FIG. 1 also apply to instrument 10 according to FIG. 2.

Dosing unit 16 of instrument 10 comprises a compartment 21 for a fluid container 22 that contains medical treatment liquid, e.g. a cell suspension with living cells or a medicinal liquid or the like. The compartment 21 can extend into housing 12. For example, fluid container 22 can be configured in the manner of a piston syringe and comprise for this purpose a cylinder 23 having a piston 24 arranged therein, the piston rod of which projects out of cylinder 23.

Figure 3:
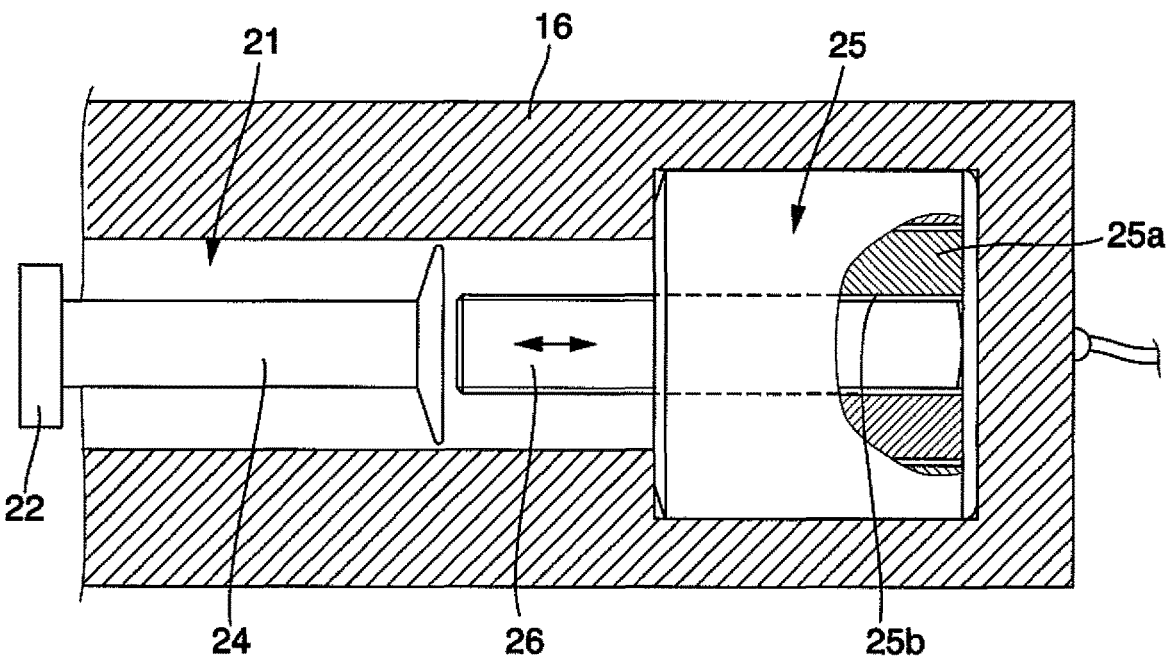

As apparent from FIG. 3, dosing unit 16 comprises a drive unit 25 that can be configured as a motor having a rotatable rotor 25a that linearly moves a plunger 26 via a gear, e.g. a spindle-type lifting gear 25*b*. Thereby drive unit 25 is particularly configured to move plunger 26 gradually in order to displace the piston in the cylinder 23 (slowly) by means of the plunger 26 via piston rod 24. A "slow" displacement of piston rod 24 thereby means such movements that do not lead to a pressure increase in fluid container 22 that is detrimental for the treatment fluid.

Figure 4:
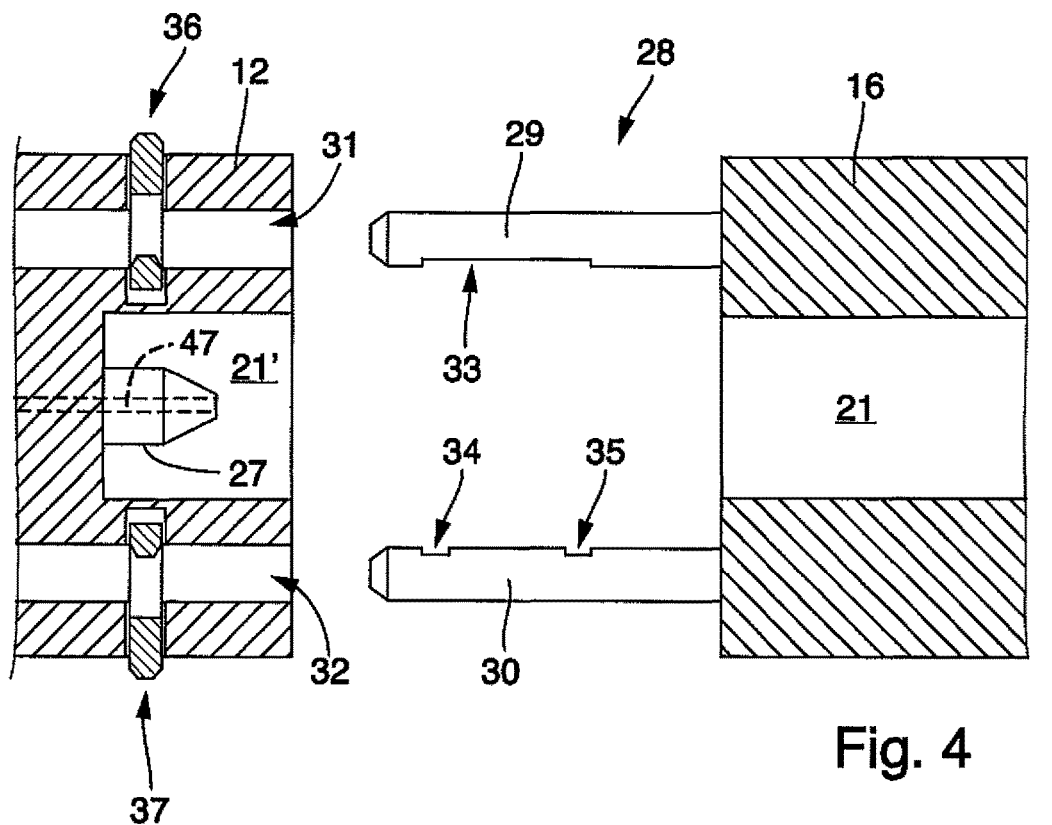

Compartment 21 extends with a section 21' into housing 12, as illustrated in FIG. 4. Inside housing 12 a connection branch 27 can be provided at the bottom of compartment 21, 21' that is suitable for connection of the fluid container 22. Connection branch 27 is only schematically illustrated in FIG. 4. In any case, connection branch 27 is configured to match with the connection of fluid container 22 in order to establish a fluid-tight connection as soon as the fluid container 22 is inserted into compartment 21 and is moved toward connection branch 27. Potential closures or sealings of fluid container 22 can thereby be penetrated.

Dosing unit 16 is particularly provided to be able to exchange fluid container 22. According to FIG. 4, for this purpose a special interface can be provided between housing 12 and dosing unit 16 that can be particularly configured to selectively keep the dosing unit 16 in abutment against housing 12, to displace it only slightly from housing 12 or to remove it entirely from housing 12.

For this purpose, dosing unit 16 can be attached to housing 12 by means of a latch coupling 28. In a simple and expedient embodiment latch coupling 28 can comprise two latch pins 29, 30, for example, to which latch openings 31, 32 are assigned that are configured in housing 12. The latch pins 29, 30 can have a circular cross-section or also any other suitable cross-section, for example an oval or polygonal cross-section, and can be provided along a part of their length respectively with recesses, i.e. for example flat areas 33, 34, 35. For example, latch pin 29 comprises a long flat area, while latch pin 30 can be provided with two short groove-like flat areas 34, 35 arranged in axial distance to one another. Latch sliders 36, 37 can be assigned to flat areas 33-35 in order to selectively lock or release latch pins 29, 30 inside latch openings 31, 32. Thereby latch sliders 36, 37 as well as flat areas 33-35 are arranged in a relation to one another, such that a release of latch slider 37 allows movement of dosing unit 16 away from housing 12 within the axial length of flat area 33. If slider 37 is locked into flat area 35, latch slider 36 is positioned at the proximal flank of flat area 33. If latch slider 37 is locked into flat area 34, latch slider 36 is positioned on the distal flank of flat area 33. Only by release of both latch sliders 36, 37, dosing unit 16 can be removed from housing 12. Flat areas and latch sliders are, however, not necessary.

The removability of dosing unit 16 from instrument 10 allows to configure instrument 10 as single-use instrument or as sterilizable instrument, whereas dosing unit 16 can be basically configured to be reused. In a modified embodiment the reusable part can, however, also comprise the housing, the handle 15 or parts thereof. Also the instrument can be configured to be entirely sterilizable.

Figure 5:
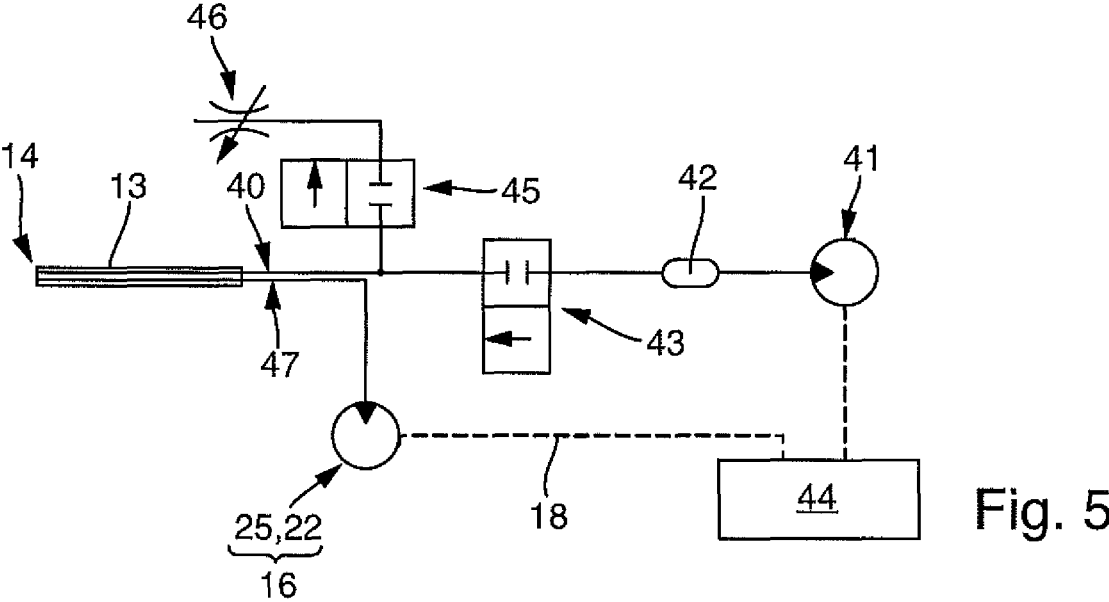

FIG. 5 illustrates the function units and components of instrument 10 and apparatus 11 in their cooperation. Thereby it is noted that some or all of the components and units of apparatus 11 described in the following can also be integrated entirely or partly in the instrument 10. However, instrument 10 at least comprises shank 13, housing 12 and dosing unit 16.

Instrument 10 comprises a first fluid channel 40 that is configured to discharge a first fluid at the distal end 14 with so high pressure and as concentrated jet that it can penetrate without the aid of an injection needle into living tissue and can open a channel in the tissue there. The first fluid is preferably and by way of example an aqueous sodium chloride solution, whereby however also other fluids can be used. The first fluid is supplied under pressure from a not illustrated reservoir by means of a pump 41 into a pressure container 42 that is connected to the first fluid channel 40 via a valve 43. The pressure container 42 can also be configured solely by the supply line, such that a separate pressure container can be omitted optionally.

The valve 43 is controlled, i.e. open-loop controlled, by means of a control device 44 and can thus be selectively opened or closed. In the rest condition (at the start of the application) valve 43 is closed. A further valve 45 closed in the rest condition branches off the fluid channel 40. It serves for pressure relief of fluid channel 40 and connects fluid channel 40 selectively via a throttle 46 with an outlet. Valve 45 and if desired also throttle 46 can be connected with control device 44 in order to be controlled by it.

The dosing unit 16 comprises particularly drive unit 25 and fluid container 22 serving as piston pump as functional components. The latter is connected to a second fluid channel 47 that extends from the branch connection 17 up to the distal end 14 of shank 13. Fluid channels 40, 47 can alternatively be joined at the distal end 14 of shank 13 inside shank 13 or inside housing 12.

The instrument 10 described so far and the apparatus 11 operate together as follows:

For start-up and preparation of an injection of treatment liquid into tissue, first dosing unit 16 is provided with the treatment liquid. For this purpose fluid container 22 is inserted into compartment 21. For simplifying or allowing this process, drive unit 25 moves plunger 26 in proximal position. This can be respectively initiated by means of control device 44 accordingly. The user can now remove dosing unit 16 partly from housing 12 by at least operating latch slider 37 and thus carry out insertion of fluid container 22 together with the piston rod of piston 24 projecting therefrom into the compartment 21. If this has been carried out, slider 37, that is latched into flat area 34 up to now, can be released and dosing unit 16 can be pushed against housing 12 until slider 37 latches into flat area 35. In doing so, fluid container 22 connects with connection branch 27, such that the fluid container 22 is now communicating with second channel 47.

In addition, control device 44 activates the pump 41 in order to fill the pressure container 42 with injection fluid and to put it under pressure. The filling of the pressure container can be part of the application process. As preparation measure in addition, first fluid channel 40 can be filled with the first fluid, i.e. the injection fluid, and thus can be vented. If this has been carried out, instrument 10 is ready for use.

Figure 6:
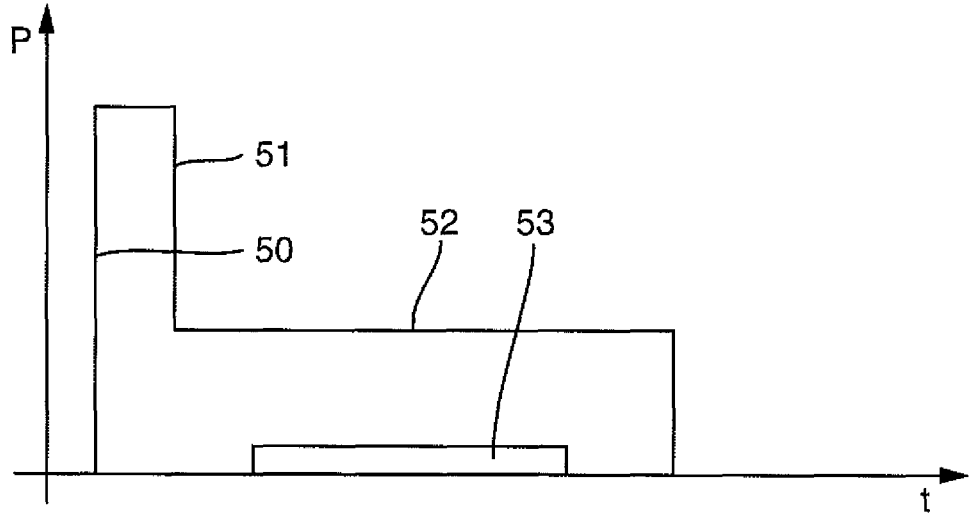

For application of the treatment liquid, shank 13 is now inserted into the body of the patient, e.g. into a lumen thereof, e.g. in the ureter or another naturally provided channel. The tissue portion into which the treatment liquid is to be applied is found by the distal end 14. If the location is reached, the first fluid (injection liquid) and the second fluid (treatment liquid) are output according to the scheme according to FIG. 6. The progress of the time-dependent pressures of the two fluids is illustrated in an idealized manner there:

First, the first fluid is discharged with a steep pressure flank 50, in that valve 43 is opened while valve 45 is closed. Thereby a sharp liquid jet is created at the distal end 14 that penetrates tissue layers and enters into the tissue. After termination of a short period (some milliseconds) valve 45 opens, whereby a decrease of the pressure in the injection fluid is carried out by means of the back flank 51. Then the first fluid is continuously supplied with a reduced pressure as indicated by curved line 52 in FIG. 6. In the meantime, control device 44 activates the drive unit 25 in order to discharge the second fluid (treatment liquid) at the distal end 14 with low pressure, as indicated in an idealized manner by curved line 53. The treatment fluid is then carried by the injection fluid and introduced into the tissue.

The injection treatment is completed thereafter. The drive unit 25 is deactivated and first the valve 43 and shortly thereafter or concurrently the valve 45 are closed.

The injection process can be again carried out in similar or identical manner at the same location or another location until fluid container 22 is emptied. Alternatively, the decrease of pressure can be realized by reduction of the conveying capacity of the pump. The valve 45 is in this case only opened for a short period for quick reduction of the pressure, i.e. with a steep back flank. Subsequently to the back flank, valve 45 is closed while valve 43 remains still opened.

For continuation of the treatment, the dosing unit 16 can be removed under appropriate use of the latch sliders 36, 37 from housing 12 in part or entirely in order to replace the fluid container 22. Thereafter the treatment can be continued as described.

The instrument 10 according to an embodiment of the invention comprises a dosing unit 16 that is connected to the handle or the housing 12 of instrument 10. In doing so, the length of the supply line for the medically effective substance to be applied is remarkably reduced compared with solutions in which the dosing unit is part of the supplying apparatus. The dosing unit 16 can substantially consist of a reusable actuator that comprises a drive unit 25 and a single-use cartridge that comprises a cylinder and a piston, for example, such as a medical syringe. The single-use cartridge can either be filled by means of the user himself/herself directly prior to the intervention or can be prefilled by the manufacturer. It is simply inserted into the instrument. For this purpose dosing unit 16 is brought into an open position offset from housing 12. This is carried out, in that latch slider 37 is operated and the dosing unit is pulled in proximal direction. After insertion of the cartridge (fluid container 22) the dosing unit can be brought in the closed position, i.e. moved toward housing 12. Thereby a fluid-tight connection between the cartridge and the second fluid channel 47 is established. Thereby the latch slider 37 locks the dosing unit 16 in this position.

The invention claimed is:

1. An instrument for injecting a liquid into tissue, the instrument comprising:

a housing on which a handle is provided for holding and guiding the instrument;

a shank that extends in distal direction and that comprises at least one fluid channel;

a fluid line that is configured for connection with a supplying apparatus for supply of the instrument with a pressurized first fluid, the pressurized first fluid having a first discharge pressure at the at least one fluid channel sufficient to open a penetration channel in the tissue and a second discharge pressure less than the first discharge pressure; and a dosing unit arranged on or in the housing, the dosing unit comprising a drive unit and a compartment adapted to receive a fluid container, the fluid container containing a second fluid, the drive unit of the dosing unit being adapted to provide a pressure application to the fluid container by reducing a volume of the fluid container to provide the second fluid at a third discharge pressure at the at least one fluid channel, the third discharge pressure being less than the first discharge pressure.

2. The instrument according to claim 1, wherein the dosing unit is releasably attached on the housing.

3. The instrument according to claim 2, wherein the shank comprises a bendable section at its distal end and wherein at least one operating element for control and bending of the shank is provided on the housing of the instrument.

4. The instrument according to claim 1, wherein the at least one fluid channel comprises a jet-focusing outlet opening at a distal end of the at least one fluid channel.

5. The instrument according to claim 1, further comprising a valve arrangement configured to create the first discharge pressure as a pressure impulse in the at least one fluid channel.

6. The instrument according to claim 1, wherein the dosing unit comprises an electrical line configured to connect to a control device.

7. The instrument according to claim 1, wherein the housing comprises:

a fluid connection for the fluid container; and a mechanical plug connection for a plug device provided on the dosing unit.

8. The instrument according to claim 7, wherein the fluid connection and the plug device have matching operation directions.

9. The instrument according to claim 1, wherein the fluid container comprises a movable piston.

10. The instrument according to claim 8, wherein the fluid container comprises a movable piston, wherein a movement direction of the moveable piston coincides with the operation direction.

11. The instrument according to claim 1, wherein the drive unit comprises a servomotor that is arranged to act on the fluid container via a gear.

12. The instrument according to claim 1, wherein the pressure application to the fluid container is independent from a pressure of the pressurized first fluid.

13. The instrument according to claim 1, wherein the at least one fluid channel comprises therein the second fluid entrained within the pressurized first fluid at a pressure less than the first discharge pressure.

14. The instrument according to claim 1, wherein the compartment for the fluid container extends from the dosing unit into the housing.

15. The instrument according to claim 1, wherein the compartment for the fluid container is formed by the housing and the dosing unit.

16. A method of using the instrument according to claim 1, the method comprising:

providing the pressurized first fluid in a pressure container;

channeling the pressurized first fluid into the at least one fluid channel at the first discharge pressure by opening a valve;

reducing a pressure of the first pressurized first fluid to the second discharge pressure;

providing the second fluid in the container;

channeling the second fluid into the at least one fluid channel line at the third discharge pressure after reducing the pressure of the first pressurized first fluid.

\* \* \* \* \*